(12) United States Patent
Benetti

(10) Patent No.: US 6,644,319 B1
(45) Date of Patent: *Nov. 11, 2003

(54) METHOD FOR CORONARY ARTERY BYPASS

(75) Inventor: Federico J. Benetti, Santa Fe (AR)

(73) Assignee: Cardiothoracic Systems, Inc., Santa Clara, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 09/660,284

(22) Filed: Sep. 12, 2000

Related U.S. Application Data

(63) Continuation of application No. 09/340,913, filed on Jun. 28, 1999, now Pat. No. 6,167,889, which is a continuation of application No. 08/889,616, filed on Jul. 7, 1997, now Pat. No. 5,947,125, which is a continuation of application No. 08/419,991, filed on Apr. 10, 1995, now Pat. No. 5,888,247.

(51) Int. Cl.[7] .............................................. A61B 19/00
(52) U.S. Cl. ..................................................... 128/898
(58) Field of Search ........................ 128/898; 623/1.11, 623/66, 2.1; 600/194, 195; 604/49–53, 107; 606/7

(56) References Cited

U.S. PATENT DOCUMENTS

| | | |
|---|---|---|
| 4,726,356 A | 2/1988 | Santilli et al. |
| 4,852,552 A | 8/1989 | Chaux |
| 5,025,779 A | 6/1991 | Bugge |
| RE34,150 E | 12/1992 | Santilli et al. |
| 5,306,234 A | 4/1994 | Johnson |
| 5,429,144 A | 7/1995 | Wilk |
| 5,452,733 A | 9/1995 | Sterman et al. |
| 5,888,247 A | 3/1999 | Benetti |
| 5,947,125 A | 9/1999 | Benetti |
| 6,026,814 A * | 2/2000 | LaFontaine et al. ........ 128/898 |
| 6,167,889 B1 * | 1/2001 | Benetti ....................... 128/898 |
| 6,311,693 B1 * | 11/2001 | Sterman et al. ............. 128/898 |
| 6,325,067 B1 * | 12/2001 | Sterman et al. ............. 128/898 |

FOREIGN PATENT DOCUMENTS

| | | |
|---|---|---|
| GB | 2267827 A | 12/1993 |

OTHER PUBLICATIONS

Acuff et al. (1996) "Minimally Invasive Coronary Artery Bypass Grafting." *Ann Thorac Surg*, vol. 61:135–137.

Akins et al. (1984) "Preservation of Interventricular Septal Function in Patients having Coronary Artery Bypass Grafts Without Cardiopulmonary Bypass." *American Heart Journal*, vol. 107(2):304–309.

(List continued on next page.)

*Primary Examiner*—David J. Isabella
(74) *Attorney, Agent, or Firm*—Alan W. Cannon; Bozicevic, Field & Francis LLP

(57) ABSTRACT

The invention comprises a method for performing a coronary artery bypass graft on a beating heart under thoracoscopic visualization without opening the chest wall. At least one small opening is formed in the patient's chest, a target artery for an arterial blood supply is located, instruments are introduced through one or more small openings formed in the patient's chest to prepare the target artery for fluid connection to the coronary artery, and instruments are introduced through one or more small openings formed in the patient's chest to connect the target artery to the coronary artery distal from a stenosis. In a preferred embodiment, a minimal left anterior intercostal thoracotomy provides access to form an anastomosis between the left internal mammary artery (LIMA) and the left anterior descending artery (LAD) while thoracoscopic viewing facilitates harvesting the LIMA. In other embodiments, access to the patient's heart may be obtained through a trocar sheath or other means for providing percutaneous access to the patient's thoracic cavity without opening the chest wall. Thoracoscopic visualization, depending on the procedure, is used to locate the arterial blood supply, the location of the coronary artery to be bypassed and the location of the occlusion in the artery. In other embodiments, the diagonal (Dx) or circumflex (Cx) arteries may be bypassed.

11 Claims, 8 Drawing Sheets

OTHER PUBLICATIONS

Akins (1994) "Controversies in Myocardial Revascularization: Coronary Artery Surgery for Single–Vessel Disease." *Seminars in Thoracic and Cardiovascular Surgery*, vol. 6(2):109–115.

Akins (1983) "Reoperation for Stenotic Saphenous Vein Bypass Grafts Without Cardiopulmonary Bypass." *The Annals of Thoracic Surgery*, vol. 35(2):201–206.

Allori (1995) "Bypass Senza Spargimento di Sangue." *Salve*, N.2:38–42.

Ancalmo et al. (1976) "A Modified Sternal Retractor." *The Annals of Thoracic Surgery*, vol. 21:174.

Archer et al. (1984) "Coronary Artery Revascularization Without Cardiopulmonary Bypass." *Texas Heart Institute Journal*, vol. 11(1):52–57.

Arsiwala et al. (1990) "Coronary Artery Bypass Grafting Without Cardiopulmonary Bypass." *Indian Heart Journal*, vol. 42(6):453–454.

Baeza et al. (1976) "Vertical Axillary Thoracotomy: A Functional and Cosmetically Appealing Incision." *The Annals of Thoracic Surgery*, vol. 22(3):287–288.

Becker et al. (1976) "Transaxillary Minithoracotomy: The Optimal Approach for Certain Pulmonary and Mediastinal Lesions." *The Annals of Thoracic Surgery*, vol. 22(3):254–259.

Beg et al. (1985) "Internal mammary Retractor." *The Annals of Thoracic Surgery*, vol. 39(1):286–287.

Benetti (1985) "Direct coronary surgery with saphenous vein bypass without either cardiopulmonary bypass or cardiac arrest." *J Cardiovasc Surg* (Torino), vol. 26(3):217–22.

Benetti (1991) "Coronary Artery Bypass Without Extracorporeal Circulation Versus Percutaneous Transluminal Coronary Angioplasty: Comparison of Costs." *The Journal of Thoracic and Cardiovascular Surgery*, vol. 102(5):802–803.

Benetti et al. (1991) "Direct myocardial revascularization without extracorporeal circulation. Experience in 700 patients." *Chest.*, vol. 100(2):312–6.

Benetti et al. (1986) "Anastomosis Mamariocoronaria Sin Circulacion Extracorporea." *Prense Medica Argen.*, vol. 73:213–215.

Benetti et al. (1995) "Coronary Revascularization with Arterial Conduits Via a Small Thoracotomy and Assisted by Thoracoscopy, Although Without Cardiopulmonary Bypass." *Cor Europaeum*, vol. 4(1):22–24.

Bonchek (1992) "Technical Considerations for Coronary Artery Bypass Without Cardioplegia," *Journal of Cardiac Surgery*, vol. 7(4):333–341.

Borst (1978) "Leftsided Thoracotomy for coronary Artery Reoperation." *Thoraxchirurgie Vaskulare Chirurgie*, vol. 26(2):95–7.

Borst et al. (1995) "Regional Cardiac Wall Immunobilization for Open Chest and Closed Chest Coronary Artery Bypass Grafting on the Beating Heart: The 'Octopus' Method." *Circulation*, vol. 92(8) Suppl:1–177.

Buffalo et al. (1985) "Direct myocardial revascularization without cardiopulmonary bypass." *Thorac Cardiovasc Surg.*, vol. 33(1):26–9.

Bugge (1990) "A New Internal mammary Artery Retractor." *Thorac. Cardiovasc. Surgeon*, vol. 38:316–317.

Burlingame et al. (1988) "Left Thoracotomy for Reoperative Coronary Bypass." *Journal of Thoracic Cardiovascular Surgery*, vol. 95:508–510.

Calafiore et al. (1994) "Composite Arterial Conduits for a Wilder Arterial Myocardial Revascularization." *Ann. Thorac. Surg.*, vol. 58:185–190.

Chaux et al. (1986) "A new Concept in Sternal Retraction: Applications for Internal mammary Artery Dissection and Valve Replacement Surgery." *Ann. Thorac. Surg.*, vol. 42:473–474.

Cheung et al. (1982) "An Alternative Approach to Isolated Circumflex Coronary Bypass Reoperations." *The Annals of Thoracic Surgery*, vol. 33:302–303.

Corso (1991) "Cardiopulmonary Bypass and Coronary Artery Bypass Graft. Are the risks necessary?" *Chest*, vol. 100(2):298–9.

Fanning et al. (1993) "Reoperative coronary artery bypass grafting without cardiopulmonary bypass." *Ann Thorac Surg.*, vol. 55(2):486–9.

Faro et al. (1982) "Left Thoracotomy for Reoperation for Coronary Revascularation." *The Journal of Thoracic and Cardiovascular Surgery*, vol. 84:453–455.

Favaloro et al. (1970) "Direct myocardial revascularization by saphenous vein graft. Present operative technique and indications." *Ann Thorac Surg.*, vol. 10(2):97–111.

Gandjbakheh et al. (1989) "Left Thoracotomy Approach for coronary Artery Bypass Grafting in patients with Pericardial Adhesions." *The Annals of Thoracic Surgery*, vol. 48:871–873.

Grinda et al. (1996) "Right Anterolateral Thoracotomy for Repair of Atrial Septal Defect." *Ann Thorac Surg.*, vol. 62:175–178.

Grosner et al. (1990) "Left Thoracotomy Reoperation for Coronary Artery Disease." *Journal of Cardiac Surgery*, vol. 5:304–308.

Horii et al. (1993) "Two–Staged Repeat Myocardial Revascularization Through the Sternal Re–Entry and the Left Thoracotomy with Coronary Anastomosis Under the Beating Heart." *Journal of the Japanese Association for Thoracic Surgery*, vol. 41(9):1511–4.

Kawase et al. (1993) "A Case of Treating Abrupt Closure Due to Post PTCA Dissection by Emergent CABG–Reoperation Via Extracorporeal Circulatory Method Conducted with the Heart 'Beating'." *Japanese Journal of Thoracic Surgery*, vol. 46(6):512–5.

Kolessov (1967) "Mammary artery–coronary artery anastomosis as method of treatment for angina pectoris." *J Thorac Cardiovasc Surg.*, vol. 54(4):535–44.

Kyobu et al. (1993) "Coronary Artery Bypass Grafting Surgery Without Cardiopulmonary Bypass." *Department of Thoracic and Cardiovascular Surgery*, vol. 4(4):598–602.

Loop et al. (1986) "Influence of the Interal–Mammary–Artery Graft on 10–Year Survival and Other Cardiac Events." *N. Eng. J. Med.*, vol. 3145(1):1–6.

Lytle et al. (1992) "Coronary Artery Bypass Surgery." *Current Problems in Surgery*, vol. XXIX(10):737–807.

Maddaus et al. (1992) "Coronary Artery Surgery Without Cardiopulmonary Bypass: Usefulness of the Surgical Blower–Humidifier." *Journal of Cardiac Surgery*, vol. 7(4):348–50.

McKeown et al. (1981) "A Modified Sternal Retractor for Exposure of the Internal Mammary Artery." *The Annals of Thoracic Surgery*, vol. 32:619.

Mitchell et al. (1976) "Simplified Lateral Chest Incision for Most Thoracotomies Other Than Sternotomy." *The Annals of Thoracic Surgery*, vol. 22(3):284–286.

Moshkovitz et al. (1993) "Coronary Artery Bypass Without Cardiopulmonary Bypass—the Pros and the Cons." *Isr. J. Med. Sci*, vol. 29:716–720.

Pfister et al. (1992) "Coronary artery bypass without cardiopulmonary bypass." *Ann Thorac Surg.*, vol. 54(6):1085–91.

Richenbacher et al. (1989) "Current Status of Cardiac Surgery: A 40–Year Review." *Journal of the American College of Cardiology*, vol. 14(3):535–544.

Robinson et al. (1995) "Minimally Invasive Coronary Artery Bypass Grafting: A new Method Using an Anterior mediastinotomy." *Journal of Cardiac Surgery*, vol. 10;529–536.

Robinson et al. (1995) "A Minimally Invasive Surgical Method for Coronary Revascularization—Preliminary Experience in Five Patients." *Circulation*, vol. 92(8):1–176.

Schwartz et al. (1996) "Minimally Invasive Cardiopulmonary Bypass with Cardioplegic Arrest: A Closed Chest Technique with Equivalent Myocardial Protection." *The Journal of Thoracic and Cardiovascular Surgery*, vol. 111(3).

Stevens et al. (1994) "Closed–Chest Coronary Artery Bypass with Cardioplegic Arrest in the Dog." *Circulation*, vol. 90(4), Part 2: 1–251.

Tector et al. (1994) "Total Revascularization with T Grafts." *Ann. Thorac. Surg.*, vol. 57:33–39.

Trapp et al. (1985) "To Use or Not to Use the Pump Oxygenator in Coronary Bypass Operations." *The Annals of Thoracic Surgery*, vol. 19(1):108–109.

Trapp et al. (1975) "Placement of Coronary Artery Bypass Graft Without Pump Oxygenator." *The Annals of thoracic Surgery*, vol. 19(1):1–9.

Ungerleider et al. (1985) "Left Thoracotomy for Reoperative Coronary Artery Bypass Procedures." *The Annals of Thoracic Surgery*, vol. 40:11–15.

Uppal et al. (1994) "Right thoracotomy for reoperative right coronary artery bypass procedures." *Ann Thorac Surg.*, vol. 57(1):123–5.

Vincent (1989) "A Compact Single Post Internal mammary Artery Dissection Retractor." *Eur. J. Cardiothorac Surg.*, vol. 3:276–277.

Walker et al. (1986) "Avoidance of Patent Anterior Grafts at Revisional Coronary Artery Surgery: Use of a Lateral Thoracotomy Approach." *Thorax*, vol. 41:692–695.

Weintraub et al. (1994) "The Impact of Additional Procedures on the Cost at Three Years of Coronary Angioplasty and Coronary Surgery in the EAST Trial." *Circulation*, vol. 90(4), Part 2: 1–91.

Westaby (1995) "Coronary Surgery Without Cardiopulmonary Bypass." *Br Heart J.*, vol. 73(3):203–5.

* cited by examiner

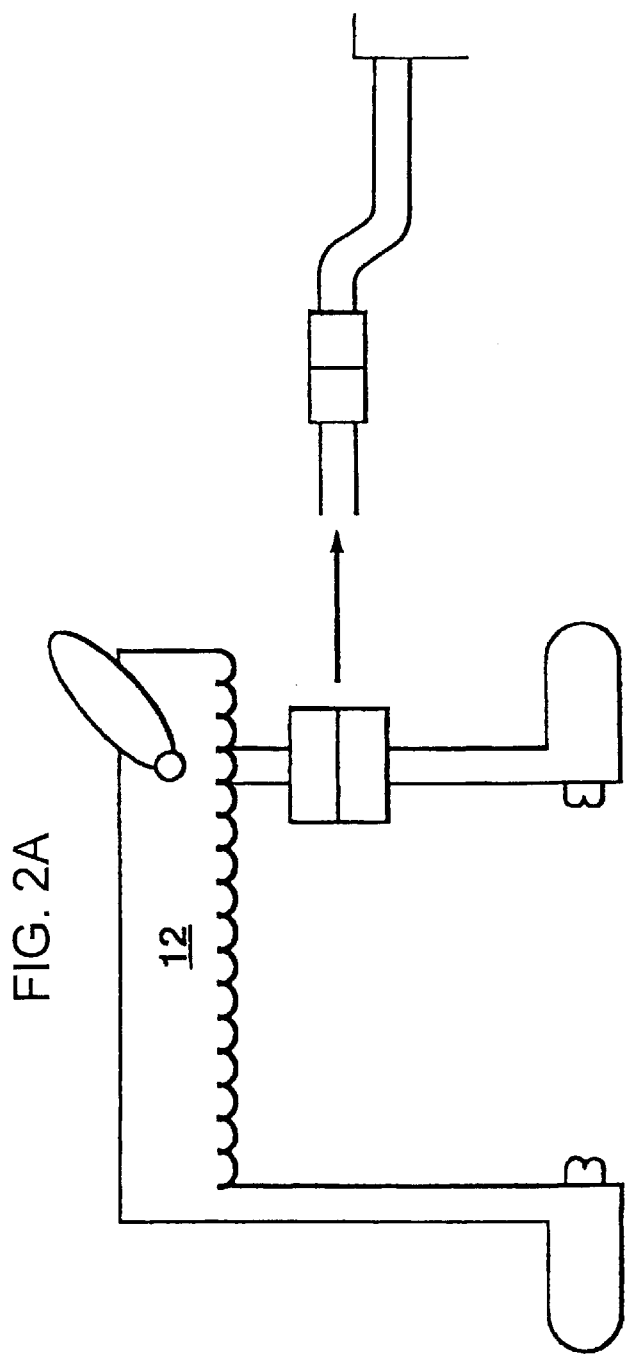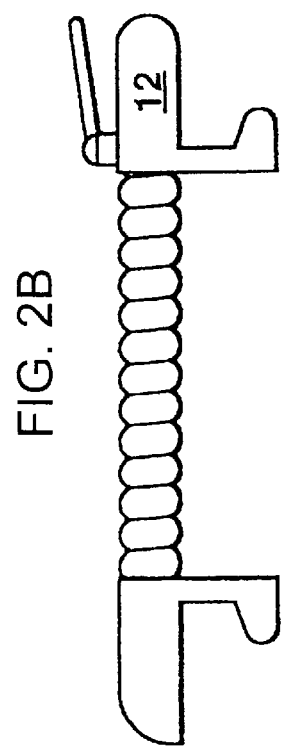
FIG. 2A
FIG. 2B

METHOD FOR CORONARY ARTERY BYPASS

This application is a continuation of application Ser. No. 09/340,913 filed on Jun. 28, 1999 which issued on Jan. 2, 2001 as U.S. Pat. No. 6,167,889, which is a continuation of application Ser. No. 08/889,616 filed on Jul. 7, 1997, which issued on Sep. 7, 1999 as U.S. Pat. No. 5,947,125, which is a continuation of Ser. No. 08/419,991 filed Apr. 10, 1995, which issued on Mar. 30, 1999 as U.S. Pat. No. 5,888,247.

BACKGROUND OF THE INVENTION

This invention is directed to a method for performing a minimally invasive coronary artery bypass graft. More particularly, the method permits a thoracoscopic procedure without the need for extracorporeal circulation or other cardiopulmonary bypass.

A coronary artery bypass graft (CABG) involves performing an anastomosis on a diseased coronary artery to reestablish blood flow to an ischemic portion of the heart muscle. Improved long-term survival has been demonstrated bypassing the left anterior descending artery (LAD) with a left internal mammary artery (LIMA). Loop, F. D., Lytle, B. W., Cosgrove, D. M., et al. "Influence of the Internal Mammary Artery on 10 Years Survival and Other Cardiac Events," *N. Eng. J. Med.,* 1986; 314:1–6. This has encouraged surgeons to extend revascularization with arterial grafts to all coronary arteries. In multiple-vessel disease, other arteries have then to be used, such as: the right internal mammary artery (RIMA), the right gastroepiploic artery, the inferior epigastric artery and the radial artery. At the same time, other techniques are also being used: arterial sequential anastomosis and/or graft elongated and/or Y- or T-grafts. Calafiore, A. M., DiGianmarco, G., Luciani, N., et al. "Composite Arterial Conduits for a Wider Arterial Myocardial Revascularization." *Ann Thorac. Surg.,* 1994:58:185–191 and Tector, A. J., Amundson, S., Schmahl, T. M., et al. "Total Revasculization With T-Grafts". *Ann Thorac. Surg.,* 1994:57:33–39.

Traditionally, bypass graft procedures have required opening the chest wall via a sternotomy, stopping the heart and supporting the patient with a cardiopulmonary bypass system. These requirements are extremely invasive, pose significant risks, require lengthy hospitalization and are expensive. In hope of overcoming these and other problems, physicians have developed a number of alternatives such as percutaneous transluminal coronary angioplasty (PTCA), atherectomy, placement of stents and pharmacological treatments. The most common of these is PTCA which offers relatively short hospitalization periods and is relatively inexpensive. However, these benefits are mitigated by a significant restenosis rate. Similarly, the other alternatives suffer from their own drawbacks.

For these and other reasons, providing an anastomosis between an internal mammary artery and the LAD may be the best therapeutic option for severe proximal lesions. Benetti, F. J., Rizzardi, J. L., Naselli, G., et al., "Anastomosis Manerio Coronaria Sin Circulatión Extracorpórea," *Prense Médica Argentina,* 1985; 73:213. Accordingly, there is a need for improved CABG procedures that simplify surgical techniques and diminish hospital stays and costs.

SUMMARY OF THE INVENTION

The invention comprises a method for performing CABG procedures without the need for opening the chest wall, stopping the heart or providing cardiopulmonary bypass. Generally, at least one small opening is formed in the patient's chest, a target artery for an arterial blood supply is located through an opening in the patient's, chest, instruments are introduced through one or more small openings formed in the patient's chest to separate the target artery from its support base; and instruments are introduced through one or more small openings formed in the patient's chest to connect the target artery to a portion of a coronary artery distal from a stenosis in fluid communication therewith to supply arterial blood from the target artery thereto. In a preferred embodiment, a minimal left anterior intercostal thoracotomy provides access to form the anastomosis between the left internal mammary artery (LIMA) and the left anterior descending artery (LAD) while thoracoscopic viewing facilitates harvesting the LIMA. In other embodiments, access to the patient's heart may be obtained through a trocar sheath or other means for providing percutaneous access to the patient's thoracic cavity without opening the chest wall. Depending on the type of access, thoracoscopic visualization is used to locate the arterial blood supply, the location of the coronary artery to be bypassed or the location of the occlusion in the artery. In other embodiments, the diagonal (Dx) or circumflex (Cx) arteries may be bypassed.

BRIEF DESCRIPTION OF THE DRAWINGS

FIG. 2A is an elevational view of a retractor useful in the practice of the invention.

FIG. 2B is an end view of the retractor shown in FIG. 2A.

DETAILED DESCRIPTION OF THE DRAWINGS

In selected cases, it may be possible to avoid the risks of sternotomy and cardiopulmonary bypass, and obtain the benefits of arterial conduits. The patient is intubated with a double-lumen endobronchial tube (not shown) that allows selective ventilation or deflation of the right and left lungs. The left lung is deflated to provide access to the heart and the LIMA. The preferred surgical position of the patient is right lateral decubitus, 30 degrees from horizontal, with the left arm above the head.

Figure 1:
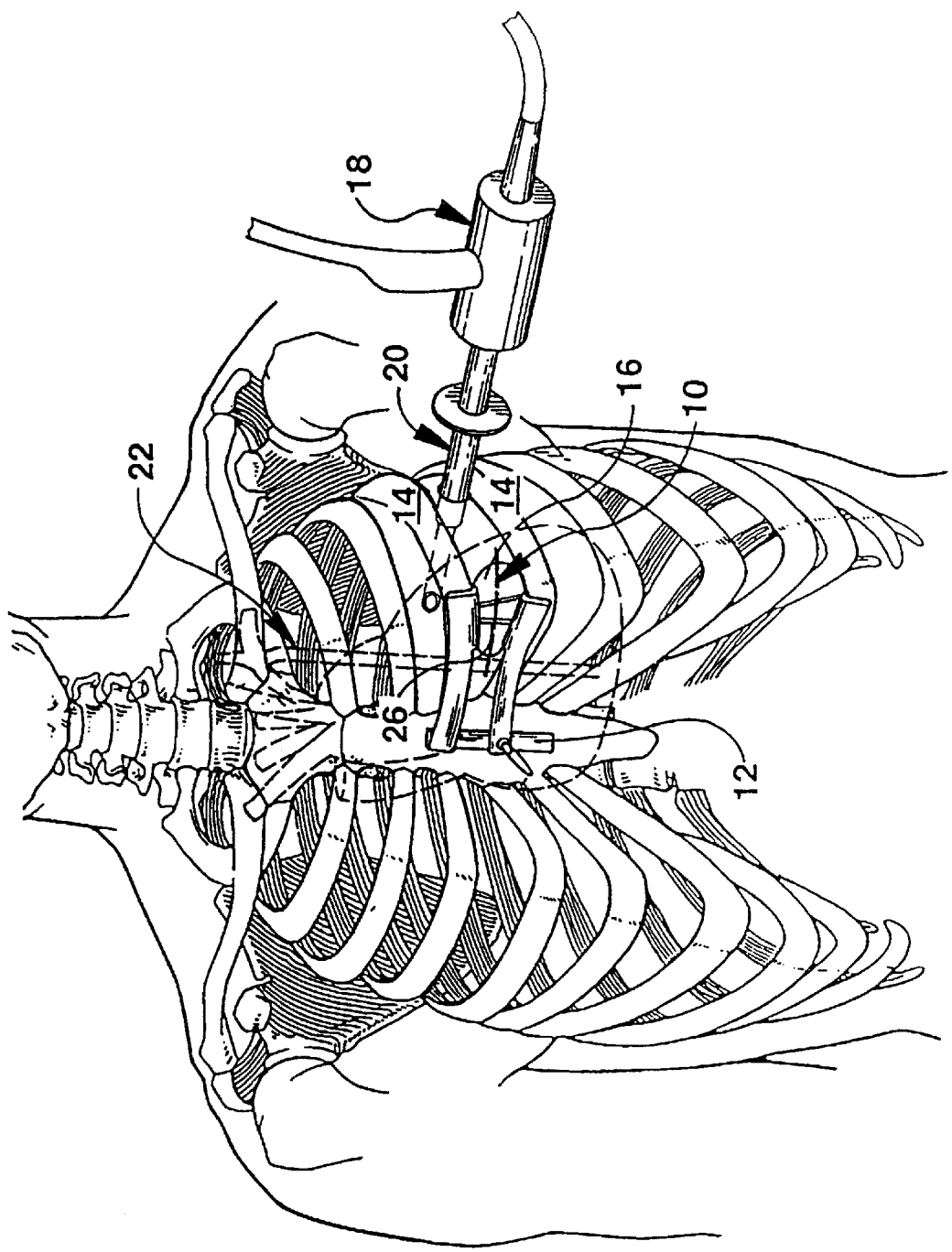
FIG. 1 is a schematic view showing placement of a thoracoscope and formation of a thoracotomy.
Figure 3:
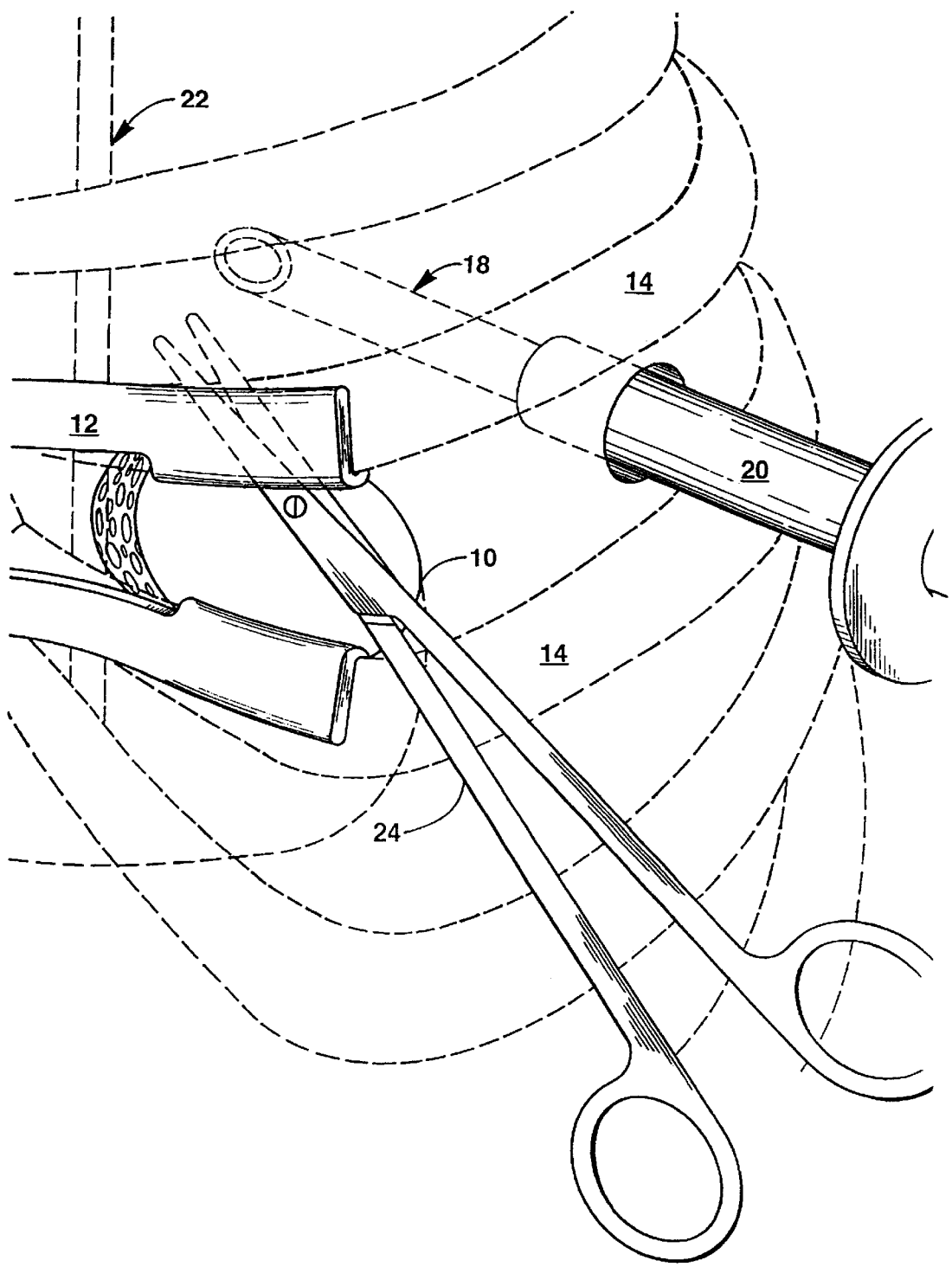
FIG. 3 is a schematic view showing dissection of the LIMA with instruments introduced through the thoracotomy.
Figure 4:
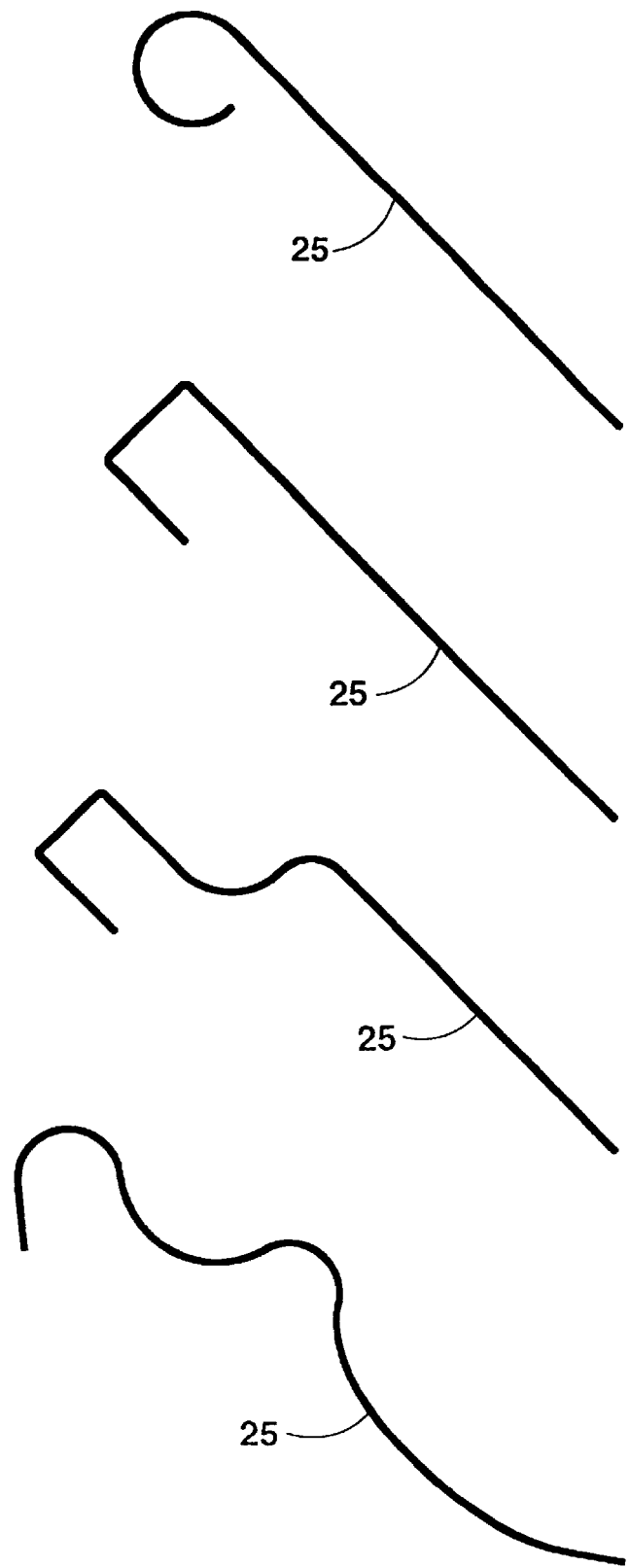
FIG. 4 shows various electrocauteries useful for dissecting the mammary artery.

Referring to FIG. 1, surgery begins with a left anterior thoracotomy 10 over the 4th intercostal space. Other sites are suitable depending on the patient's physiology, particularly the 5th intercostal space. Retractor 12 spreads ribs 14 to provide access to beating heart 16. FIGS. 2A–2B shows a special small retractor 12 which can spread the chest both horizontally and vertically. The size of thoracotomy 10 varies depending on the patient, but generally is less than 12 cm. The parietal pleura is dissected and separated from the ribbons, trying to keep it closed, to permit the introduction of thoracoscope 18 through trocar 20 at the 4th intercostal space, medial axillary line. The thoracoscope may be introduced through other areas such as the 5th through 7th intercostal spaces, again depending on the patient's physiology. Thoracoscope 18 is positioned to provide visualization of the LIMA 22. As shown in FIG. 3, instrument 24 is introduced through thoracotomy 10 to dissect LIMA 22. Instrument 24 generally comprises scissors, clip appliers, electrocauteries and other conventional devices useful for the dissection. FIG. 4 shows a variety of electrocauteries 25 useful in the practice of the invention. In some embodiments, it is useful to make a graft with a radial artery coming out from the LIMA in a T-form. This allows the formation of anastomoses with multiple coronary arteries such as sequential grafts to the Dx and Cx arteries.

Following dissection of the LIMA 22, a small pericardial incision is made to expose LAD 26. Access to the LAD and Dx arteries is relatively easy, requiring an incision of about 5 cm. Access to the Cx artery depends on the patient's characteristics and location of the vessels. In some cases, a graft to the Cx artery requires increased rotation of the patient to the right lateral decubitus and some extension of the pericardial incision. Heparin, or other suitable anticoagulant, may be administered to the patient in an appropriate dose such as 1.5 mg/kg.

Figure 5:
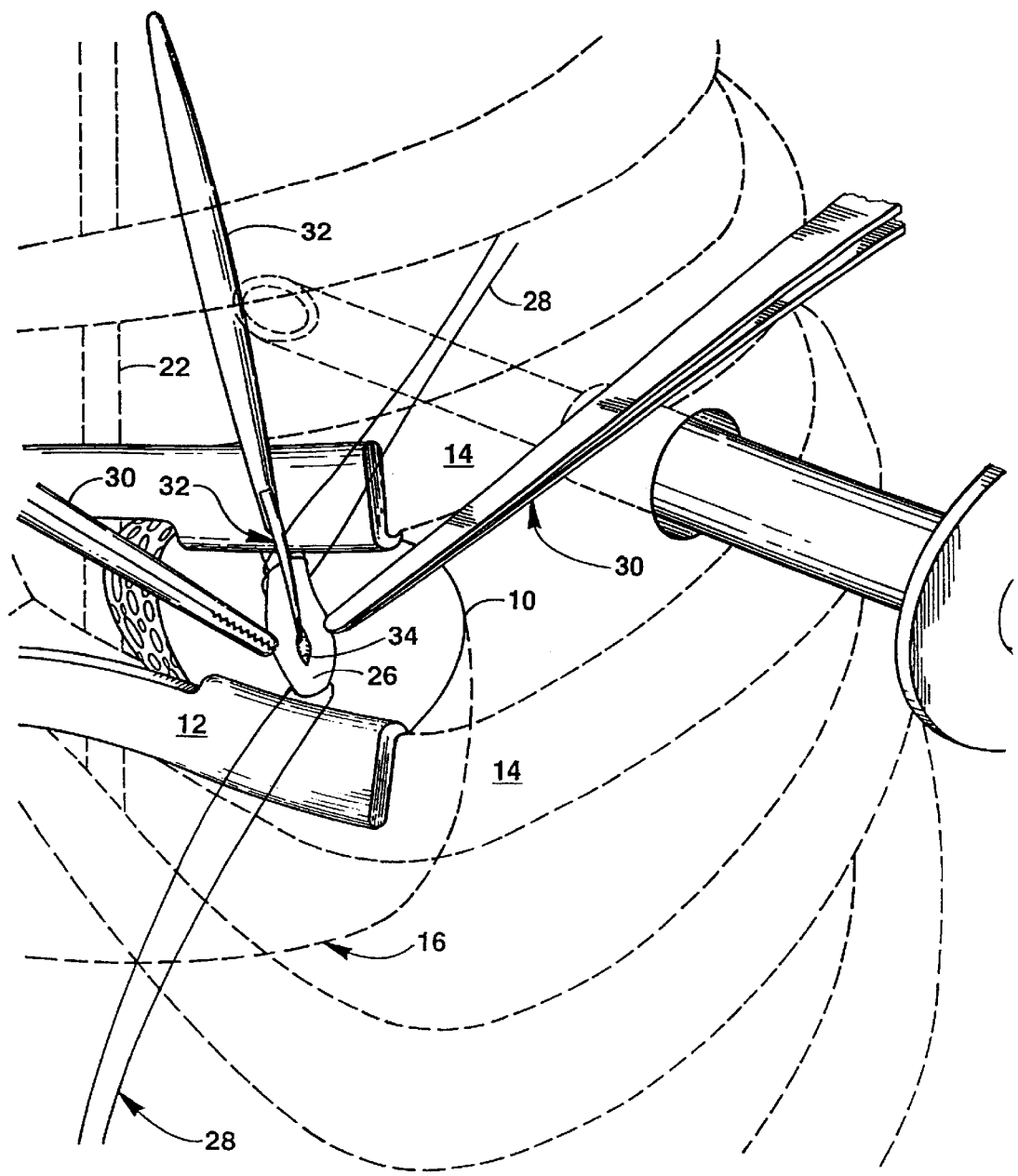
FIG. 5 is a schematic view showing instruments used to make an arteriotomy in the LAD introduced through the thoracotomy.
Figure 6:
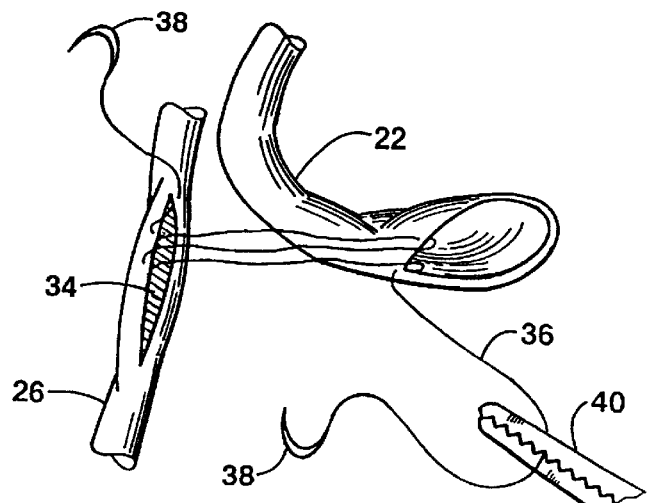
FIGS. 6–10 show the formation of the arteriectomy and the suturing of the LIMA to the LAD to provide an anastomosis.
Figure 7:
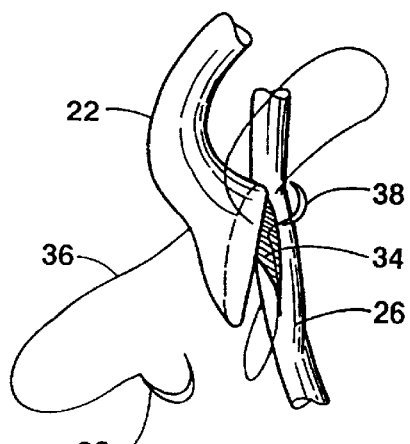
Figure 8:
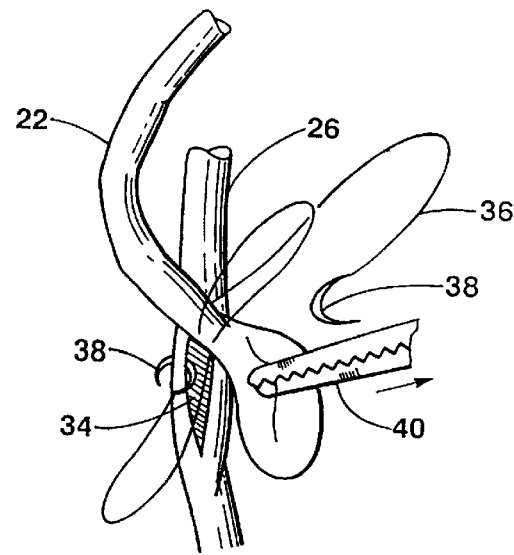
Figure 9:
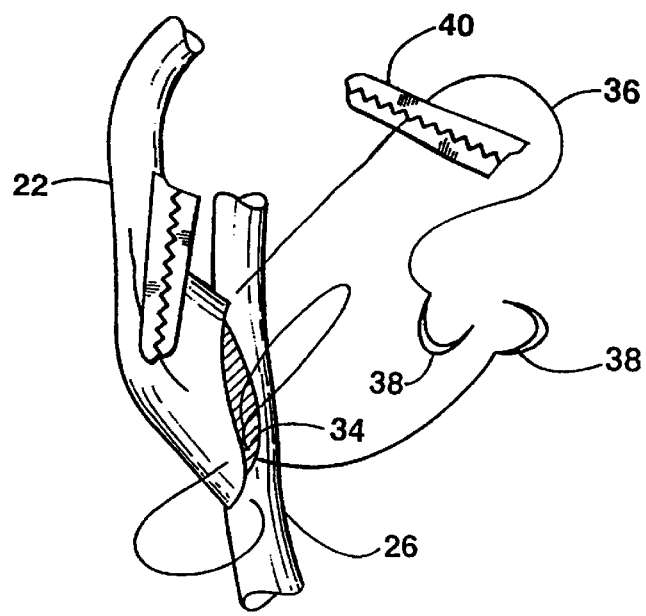
Figure 10:
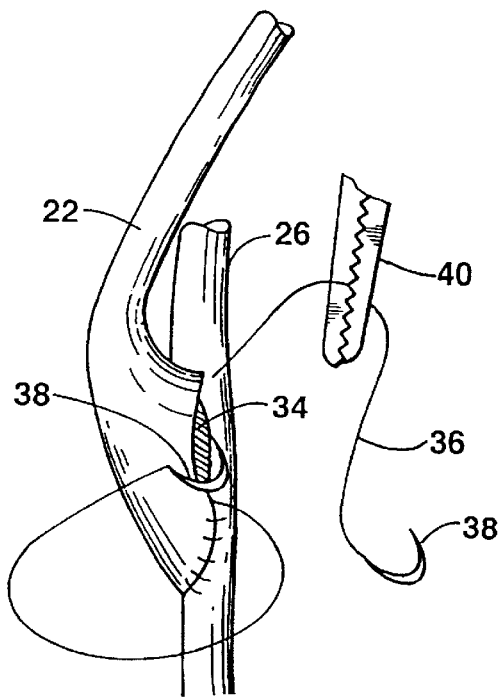

To prevent excess bleeding and to partially stabilize the vessel, a segment of LAD 26 is occluded with ligating stay sutures comprising 2.5 cm lengths of 5/0 polypropylene 28 or other appropriate ligature material as shown in FIG. 5. Applying tension to the ligatures 28 helps stabilize LAD 26 even though heart 16 is beating. Other conventional means for occluding and stabilizing the artery may be suitable. Forceps 30 are introduced through thoracotomy 10 to further stabilize and retract LAD 26. Scalpel 32 is then introduced to form arteriotomy 34 in LAD 26. As shown in FIGS. 6–10, the anastomosis between LIMA 22 and LAD 26 is formed by suturing with 7/0 polypropylene 36 and needle 38 manipulated by forceps 40. Other conventional means may be used as well. Preferably, the anastomosis is formed with a continuous suture and the aid of a conventional blower device (not shown). Further details of the blower are discussed in Tech K.H.T., Panos, A. L., Harmantas, A. A., et al. "Optimal Visualization of Coronary Artery Anastomosis by Gas Jet," *Ann, Thorac. Surg.*, 1991.

Upon completion of the anastomosis, the anticoagulant is reversed by suitable means such as prolamine. The hemostasis should be carefully controlled. The thoracotomy is closed in by conventional means; the surgery does not require resection of the costal cartilage. If the pleura is closed, a small tube for drainage may be left in place and removed the same day as surgery. If the pleura is open, a larger tube should be left in place for 24 hours. All drainage tubes are introduced through the small incision for the thoracoscope.

Figure 11:
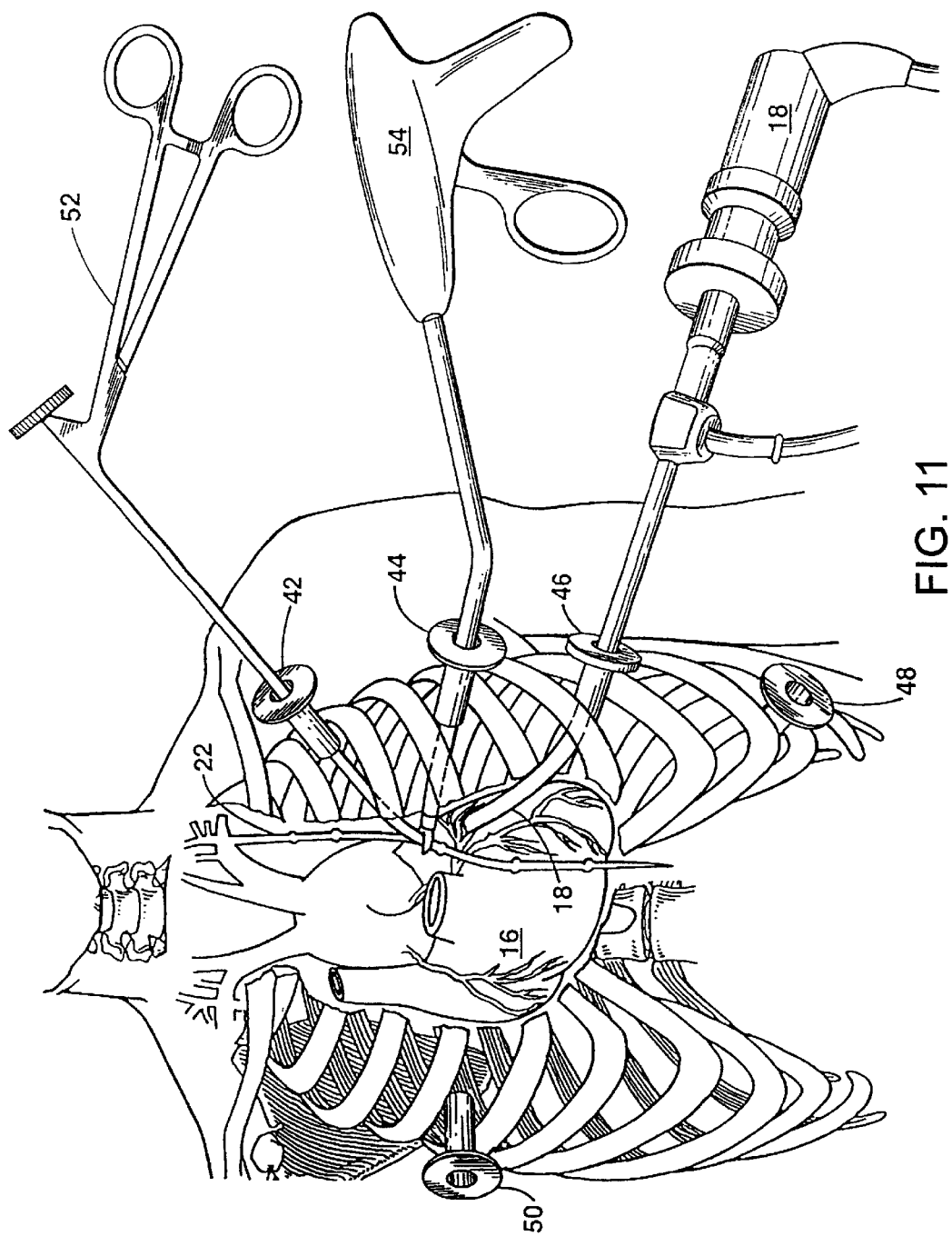
FIG. 11 is a schematic view of instruments for performing the bypass introduced through trocars without a thoracotomy.

FIG. 11 shows a series of trocars 42, 44, 46, 48 and 50 useful in the practice of the invention. In this embodiment, a thoracotomy is not necessary. Instruments 52 and 54 are introduced through the trocars to perform the dissection of the LIMA, the arteriotomy of the LAD and the formation of the anastomosis. Instruments 52 and 54 are conventional and include electrosurgical tools, graspers, forceps, scalpels, electrocauteries, clip appliers, scissors, etc. Although the trocars shown are introduced through the intercostal spaces, other points of access to the thorax may be suitable, such as parasternal punctures, midclavicular line punctures and a subxyphoid puncture.

EXAMPLES

The method of this invention was used to revascularize 10 patients from May to November 1994, one of them being a reoperation (a previous saphenous graft to LAD 11 years before). Sex was male/female in a proportion of 9/1. Age varied from 53 to 74, with an average of 61. Seven patients presented unstable angina, the other 3 suffering from stable angina. Pulmonary function was good in 8 patients, moderate in 1 and severely affected in 1. Four had previous myocardial infarction in other territories.

Access to the heart was through a small thoracotomy over the fifth left intercostal space and a thoracoscope was introduced through the fifth through seventh left intercostal space, medial axillary line, depending on the configuration of the patient's thorax. Eight patients were bypassed with a LIMA graft to LAD, the other two received triple grafts: LIMA to LAD plus a T-graft with radial artery, from the LIMA sequentially to the Dx and Cx arteries.

Mortality, morbidity and perioperative myocardial infarction have been 0% Six patients were extubated at the operating room. In 5, the pleura was maintained closed. Two patients were discharged from hospital 24 to 36 hours post-surgery; six patients were discharged between 36 and 72 hours; the other 2 were discharged 5 and 6 days post-surgery due to longer recovery time (both were patients with previous acute myocardial infarcts.) No blood transfusions were required. A new coronary angiography was done in 4 patients to monitor the patency of the grafts. Patency of the mammary artery graft was 100% when the patient was restudied before hospital discharge.

The drawings and examples are primarily directed to a graft involving the LIMA and the LAD, the Dx and the Cx arteries; nevertheless, this invention is suitable for many other graft possibilities. For example, other coronary arteries that may be bypassed include the obtuse marginal, the ramus intermedius, the right coronary, the posterior descending and others. Arteries other than the LIMA may be used to provide the arterial blood supply, such as the right internal mammary artery, the gastroepiploic artery and other arteries. Using a free graft shunt using a harvested vein or artery or a synthetic graft to form anastomoses between the aorta and the target coronary artery is also possible. Although intercostal thoracotomies are described to provide access to the heart, in some situations it may be desirable to remove a portion of a rib to improve access. Additionally, the methods of this invention can also be practiced with the use of extracorporeal circulation, making a femoro-femoral cannulation (even percutaneously) to assist the patient for a few minutes during the anastomosis. These and other modifications that would be apparent to one skilled in the art are within the scope of this invention, which is to be limited only by the claims.

What is claimed is:

1. A method for performing a coronary artery bypass graft procedure on a beating heart, said method comprising the steps of:

introducing at least one trocar into a chest cavity in which the beating heart is contained;

inserting a tool through one of the at least one trocars and forming an arteriotomy distal to a stenosis in a coronary artery of the beating heart; and inserting a tool through one of the at least one trocars and performing an anastomosis at the site of the arteriotomy.

2. The method of claim 1, wherein a plurality of trocars is inserted.

3. The method of claim 1, wherein said at least one trocar is introduced intercostally.

4. The method of claim 1, wherein said at least one trocar is introduced parasternally.

5. The method of claim 1, wherein said at least one trocar is introduced through a midclavicular line puncture.

6. The method of claim 1, wherein said at least one trocar is introduced through a subxyphoid puncture.

7. The method of claim 1, further comprising the step of stabilizing the beating heart.

8. The method of claim 1, further comprising the step of dissecting the internal mammary artery with one or more tools inserted through the at least one trocars; and wherein said anastomosis joins the internal mammary artery with the coronary artery.

9. A method for performing a coronary artery bypass graft procedure on a beating heart, said method comprising the steps of:

introducing a plurality of trocars into a chest cavity in which the beating heart is contained;

locating a target artery having an arterial blood supply;

inserting at least one tool through at least one of the trocars to perform a dissection of the target artery;

inserting a cutting tool through one of the trocars and forming an arteriotomy distal to a stenosis in a coronary artery of the beating heart; and performing an anastomosis between the dissected artery and the coronary artery by access through at least one of the trocars.

10. The method of claim 9, further comprising the step of stabilizing the beating heart.

11. The method of claim 10, wherein said stabilizing is performed at least during the performance of the anastomosis.

* * * * *